_(12)_ United States Patent
Sekiguchi et al.

(10) Patent No.: US 8,205,990 B2
(45) Date of Patent: Jun. 26, 2012

(54) FUNDUS CAMERA

(75) Inventors: Kyoji Sekiguchi, Utsunomiya (JP); Motoya Takai, Nagareyama (JP); Toshifumi Masaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 183 days.

(21) Appl. No.: 12/831,145

(22) Filed: Jul. 6, 2010

(65) Prior Publication Data

US 2011/0007272 A1    Jan. 13, 2011

(30) Foreign Application Priority Data

Jul. 9, 2009   (JP) ................................ 2009-162848

(51) Int. Cl.
*A61B 3/14*    (2006.01)
(52) U.S. Cl. ...................................................... 351/206
(58) Field of Classification Search .................. 351/206, 351/221, 205, 246
See application file for complete search history.

(56) References Cited

U.S. PATENT DOCUMENTS 7,306,336 B2 *   12/2007   Akita et al. .................. 351/206
7,458,684 B2 *   12/2008   Fukuma et al. ............... 351/205

FOREIGN PATENT DOCUMENTS

JP   08-150121 A   6/1996

* cited by examiner

*Primary Examiner* — Hung Dang
(74) *Attorney, Agent, or Firm* — Canon U.S.A. Inc., IP Division

(57) ABSTRACT

A fundus camera that obtains focus evaluation values by scanning, in which a focusing lens moves a predetermined distance according to a photographing mode before the focusing lens starts scanning for obtaining focus evaluation values.

8 Claims, 8 Drawing Sheets

FUNDUS CAMERA

BACKGROUND OF THE INVENTION

1. Field of the Invention

The present invention relates to a fundus camera having an automatic focusing function.

2. Description of the Related Art

Japanese Patent Application No. 08-150121 discusses a fundus camera in which either a visible light mode or a near-infrared light mode is selected for observation of fundus, and an automatic focusing is performed based on a fundus image for photographing the fundus image using visible light.

Conventionally, in auto-focusing by a sharpness detection system, focus evaluation values are obtained based on high frequency components within a predetermined area of a fundus image while moving a focusing lens. The curve profile (mountain shape) of changing values needs to be obtained to perform auto-focusing.

To obtain the profile and a peak of a curve, a focusing lens is controlled as follows: first, a focusing lens moves between a − endpoint and a + endpoint (in either direction) within a moving range for scanning to obtain focus evaluation values, so that a peak of the profile of the scanned focus evaluation values is detected. After the detection, when the following focus evaluation value drops below a predetermined value, the scanning is stopped. Then, the focusing lens returns to the position where the peak value of the focus evaluation values can be acquired, and photographing is performed thereat.

FIG. 8 illustrates the above control. The horizontal axis represents moving range of a focusing lens between a + end point for the limit of a + diopter and a − end point for the limit of a − diopter. The vertical axis (on the + side) represents focus evaluation value, each of which is, for example, a sum of values for high frequency components within a predetermined area of a fundus image.

With respect to an image, the contrast is higher and thus the focus evaluation values are higher at the positions closer to the in-focus position of an image. The curves in FIG. 8 consists of focus evaluation values for a case where a focusing lens is moved throughout the moving range for scanning. Actually, however, apart of the range is scanned, resulting in a curve only for the range.

The vertical axis (on the − side) represents time with respect to movement of a focusing lens and a sequence of scanned focus evaluation values. The solid line Mx represents a simple movement of a focusing lens, and the broken line Sx represents scanning for acquiring focus evaluation values, wherein x is the order of movement.

In FIG. 8, each control of a focusing lens starts at the position marked by a double circle, and ends at the position marked by a circle. The position marked by the triangle on the horizontal axis represents the position of a focusing lens in the previous focusing sequence. In the case of FIG. 8, the focusing lens was moved as illustrated in M1, S1, and M2 in this order for photographing.

So far, however, no fundus camera has come into use in which the controls of automatic focusing in a visible-light observation mode and a near-infrared light observation mode are optimized to reduce the time required for automatic focusing.

SUMMARY OF THE INVENTION

The present invention is directed to a fundus camera capable of reducing the time required for automatic focusing by performing appropriate control of an automatic focusing according to a photographing mode.

According to an aspect of the present invention, A fundus camera includes an observation photographing optical system having a focusing lens for focusing an image of a fundus of a subject's eye onto an image capturing unit, a photographing mode selection unit configured to select a photographing mode, and a control unit configured to control a position of the focusing lens based on focus evaluation values calculated using the fundus image on the image capturing unit, wherein the control unit switches moving operations of the focusing lens according to the photographing mode.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
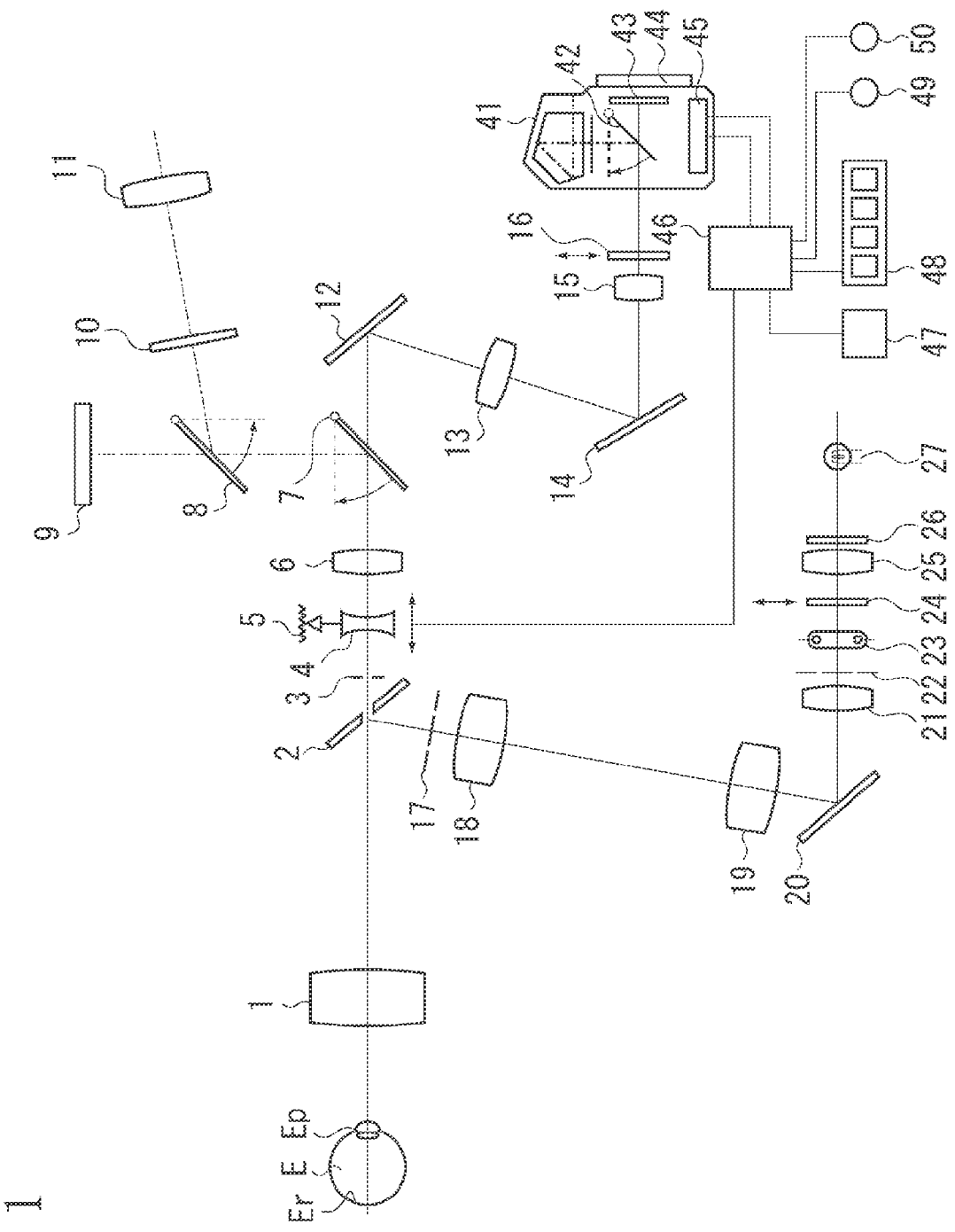
FIG. 1 illustrates a configuration of a fundus camera.

FIG. 1 illustrates a configuration of a fundus camera according to the present exemplary embodiment. The fundus camera is provided with an observation photographing optical system which is positioned opposite to a subject's eye E. The observation photographing optical system includes, in sequence, an objective lens 1, an aperture mirror 2 located approximately conjugate to the pupil Ep of the subject's eye E, a diaphragm 3, a focusing lens 4, and a potentiometer 5 for detecting a position of the focusing lens 4. The observation photographing optical system further includes an imaging lens 6, a dichroic flip-up mirror 7 for transmitting near-infrared light but reflecting visible light, fixed mirrors 12 and 14, and relay lenses 13 and 15. Following the relay lenses, an infrared cut filter 16 is inserted in the optical path during photographing, and a digital camera 41 is disposed at the end of the optical path for observation and photographing of a fundus image.

Along the optical axis of light reflected by the flip-up mirror 7, a viewfinder optical system including a movable mirror 8, a field stop 10, and an eye-piece lens 11, and an internal fixation lamp 9 are arranged.

The digital camera 41 is mounted to the body of the fundus camera using a removable mount. The digital camera 41 has a quick-return mirror 42, a CMOS area sensor 43, an LCD monitor 44, a processing circuit 45.

The CMOS area sensor 43 is provided with an RGB filter that passes near-infrared radiation, and is sensitive to visible and infrared light to capture moving and static images. To capture moving images, an amplifier in the CMOS area sensor 43 is set to high gain to generate thinned images suitable for a resolution of the LCD monitor 44 by a processing circuit 45, and the resultant moving images are displayed on the LCD monitor 44.

For photographing a fundus, light is emitted from a xenon tube 23 to capture a still image of the fundus. In this case, the amplifier in the CMOS area sensor 43 is set back to normal for obtaining a higher S/N. The resulting image data having the resolution of the CMOS area sensor 43 for every pixel is developed by the processing circuit 45, and stored in a storage medium (not illustrated) in a specified file format.

Figure 6:
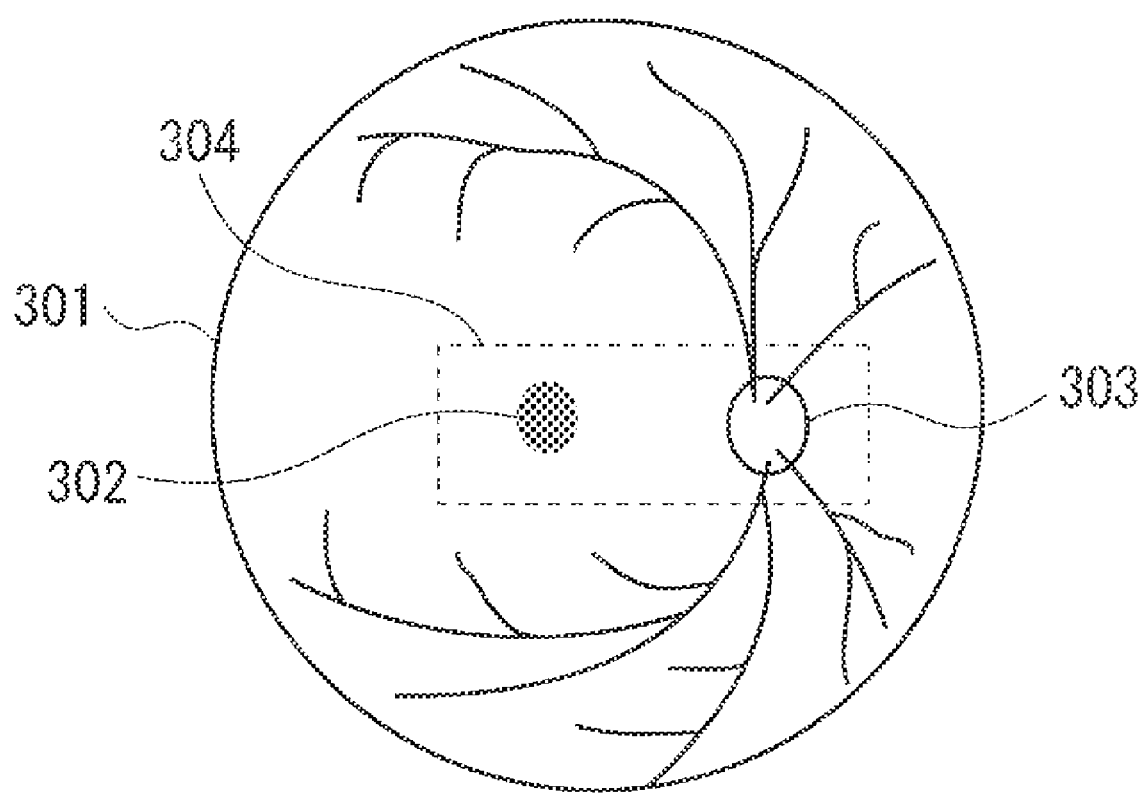
FIG. 6 illustrates a range for calculating focus evaluation values.

FIG. 6 illustrates an area for calculating contrast of a fundus image. A fundus image 301 is formed on the CMOS area sensor 43, and contains a macula 302 and an optic disk 303. Contrast of the image is calculated for the area 304. The processing circuit 45 calculates a focus evaluation value, which represents a focusing level of the moving image to be photographed, by adding signals within a range of a bandwidth that is further limited from the high frequency components of the area 304 in the moving image.

The focusing lens moves within a moving range to obtain focus evaluation values, and the focus evaluation value at each point within the range is complemented using, for example, a spline curve to produce a curve, so that the peak of the curve is calculated as an in-focus position. The control unit 46 of the fundus camera controls the focusing lens to move based on the resultant calculation. The quick-return mirror 42 in the digital camera 41 is held in a flipped state during photographing.

If no input operation is detected for a predetermined time, the control unit 46 controls the focusing lens 4 to move to the approximately central position (0 diopter) within the moving range. The control unit 46 controls the photographing to be performed at a in-focus position moved from a predetermined direction and stopped to reduce the influence of backlash of the driving mechanism of the focusing lens 4, and to maintain focusing accuracy.

In the present exemplary embodiment, the focusing lens 4 simply moves from the + end point to the − end point, and scans for acquiring focus evaluation values from the − end point to the + end point. The directions, however, may be reversed. During the scanning for acquiring focus evaluation values, the focusing lens 4 may be moving at a low speed, or may stop intermittently to obtain each focus evaluation value.

In the former case, the speed needs to be slow enough so that the distance in which the focusing lens 4 moves while obtaining a focus evaluation value does not impair focusing accuracy. In the latter case, a higher speed may be used, but this involves abrupt acceleration and sudden stop, which resulting in vibration. Accordingly, in either case, the focusing lens 4 can move for scanning to obtain focus evaluation values at a slower speed than that for simple moving.

On the illumination optical path along incident light to the aperture mirror 2, the following components are arranged in sequence toward the aperture mirror 2: a halogen lamp 27 that is a light source for observation of fundus; a diffusion plate 26; a condenser lens 25; a visible-light cut filter 24; a xenon tube 23 that is located approximately conjugate to a pupil Ep of a subject's eye E; a ring slit 22; a condenser lens 21; a fixed mirror 20; relay lenses 18 and 19; and a cornea baffle 17.

For fundus observation, a light beam is emitted from the halogen lamp 27 and passes through the visible-light cut filter 24, so that a fundus is illuminated with the transmitted near-infrared light. For photographing, the halogen lamp 27 is turned off, and light is emitted from the xenon tube 23 to illuminate the fundus.

The control circuit 46 controls insertions and retractions of the flip-up mirror 7, the movable mirror 8, the filters 16 and 24, and positioning of the focusing lens 4, and communication with the digital camera 41. The control circuit 46 is also connected to a photographing switch 50, a right/left eye detection switch 49 for detecting a direction of an eye to be photographed, a photographing mode switch 48, and a storage circuit 47 that stores a position of the focusing lens in database for each mode or each photographing with date and on a week-to-week basis.

The positional data in the database can be used, for example, as a distribution of photographing for a month in a photographing mode, so that the focusing lens 4 is moved to a position according to the data. The optical system of the fundus camera is mounted in a housing. When the housing is moved to be adjusted to a subject's right/left eye, the right/left eye detection switch 49 is turned on/off to detect the direction of the eye to be photographed.

In the fundus camera having the above described configuration, the photographing mode switch 48, which is a photographing mode selection unit, is used to select one of a mydriatic photographing mode and a non-mydriatic photographing mode. When the mydriatic photographing mode is selected, the visible-light cut filter 24 retracts from the optical path, and the infrared cut filter 16 is inserted in the optical path.

For automatic focusing, the flip-up mirror 7 retracts from the optical path. A light beam is emitted from the halogen lamp 27 to pass through the infrared cut filter 16. The transmitted visible light beam passes through the ring slit 22 and the condenser lens 21, is reflected by the fixed mirror 20 and the aperture mirror 2 around the aperture to pass through the objective lens 1 to the pupil Ep of the subject's eye E. Then, the visible light beam is incident on the fundus Er to illuminate the fundus with the visible light.

The light beam is reflected by the fundus Er to pass through the center of the pupil Ep, the objective lens 1, the aperture of the aperture mirror 2, the diaphragm 3, and the focusing lens 4 to be reflected by the fixed mirrors 12 and 14, and pass through the infrared cut filter 16. The light beam is focused onto the CMOS area sensor 43 in the digital camera 41 for capturing an image.

When the non-mydriatic photographing mode is selected using the photographing mode switch 48, which is a selection unit, the visible-light cut filter 24 is inserted into the optical path, and the flip-up mirror 7 moves into the optical path. The movable mirror 8 shifts to the position illustrated by the broken line, and the infrared cut filter 16 retracts from the optical path.

A light beam is emitted from the halogen lamp 27 to pass the infrared cut filter 16, where a near infrared range of the beam is extracted. The extracted near-infrared light beam is similarly reflected by the aperture mirror 2 around the aperture to pass through the objective lens 1 to illuminate the fundus Er of the subject's eye E. The near-infrared light beam is reflected by the fundus Er to pass through the objective lens 1, the center of the aperture mirror 2, the focusing lens 4, and the flip-up mirror 7, which is a dichroic mirror.

The light beam is then reflected by the fixed mirrors 12 and 14 to be focused on the CMOS area sensor 43 for capturing an image. A fundus image captured in the CMOS area sensor 43 is displayed on the LCD 44 as a moving image. An operator can perform alignment using a control stick (not illustrated).

In the non-mydriatic mode, with the movable mirror 8 being retracted from the optical path, a visible light beam from the internal fixation lamp 9 is reflected by the flip-up mirror 7, and passes through the focusing lens 4, the center of the aperture mirror 2, and the objective lens 1 to be projected onto the fundus. Thus, a subject's eye can stare at the turned-on light source image of the internal fixation lamp 9. The direction of the fundus is controlled by adjusting the light emitting position of the internal fixation lamp 9 using a switch (not illustrated). In the mydriatic mode, the other eye, which is not a subject's eye, is controlled to stare at an external fixation lamp (not illustrated), and the position of the fundus is adjusted.

When a finder is used in the mydriatic mode, the flip-up mirror 7 and the movable mirror 8 are inserted into the optical path by operating a switch (not illustrated). A visible light beam reflected by a fundus is reflected and guided by the flip-up mirror 7 and the movable mirror 8 into the viewfinder optical system. The light beam from the fundus does not enter the digital camera 41, and thereby no automatic focusing control is performed. Focus adjustment of the optical system is performed by rotating a knob (not illustrated) to move the focusing lens 4.

When the fundus is aligned with the optical system and the photographing switch 50 is half pressed, the control unit 46 causes the focusing lens 4 to move in the direction of – diopter values (– direction) by a predetermined distance and then to move for scanning in the direction of + diopter values (+ direction) to obtain focus evaluation values. The predetermined distance is determined according to a photographing mode.

Focusing control will be described below with reference to FIG. 2. When focusing is completed, the completion is notified to the operator by a display (not illustrated) or sound, so that the operator fully presses the photographing switch 50 to flip up the flip-up mirror 7. This operation is required in the cases where a finder is used in the non-mydriatic mode or the mydriatic mode. As a result, the infrared cut filter 16 is inserted into the optical path (in the non-mydriatic mode) for photographing using light from the xenon tube 23.

The peak position of the focus evaluation values in the non-mydriatic mode is corrected by moving the focusing lens 4 before light is emitted for photographing, because the focusing position is different from that in mydriatic mode, which uses visible light for fundus illumination, and slightly behind the retina Er.

Figure 2A:
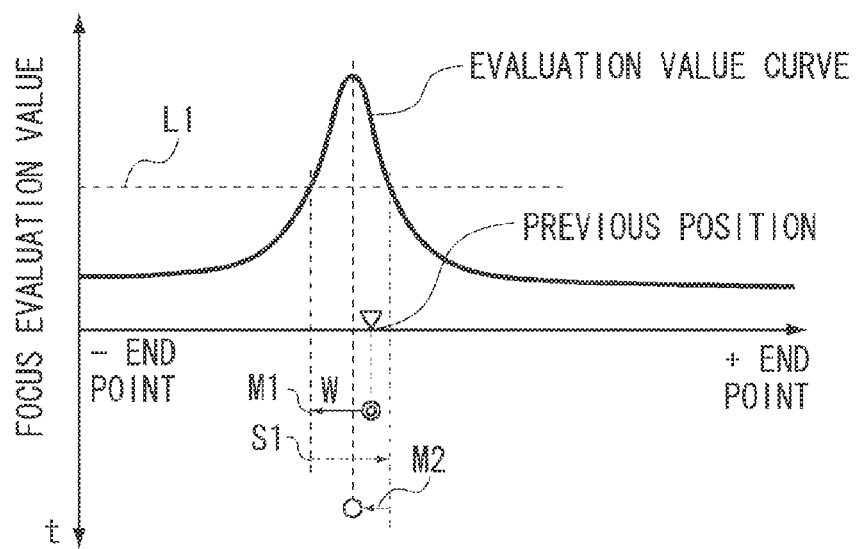
FIGS. 2A and 2B illustrate operations of a focusing lens.
Figure 2B:
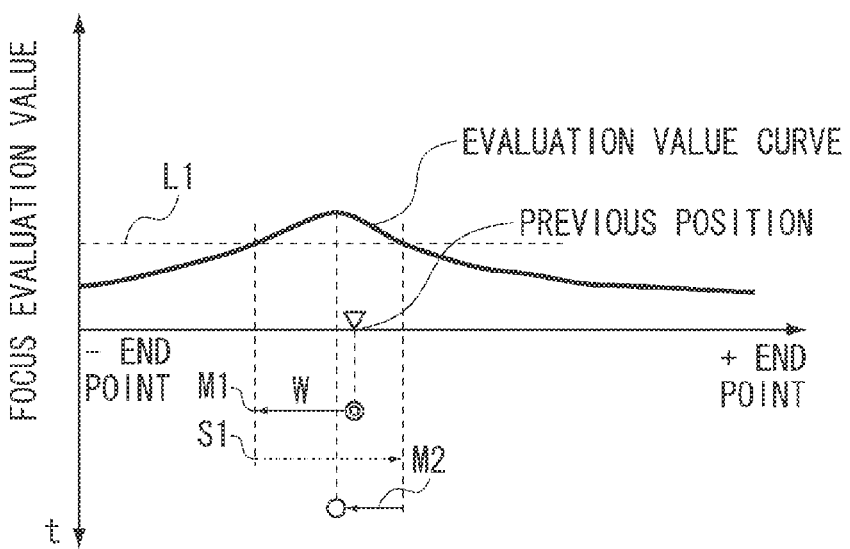
Figure 3A:
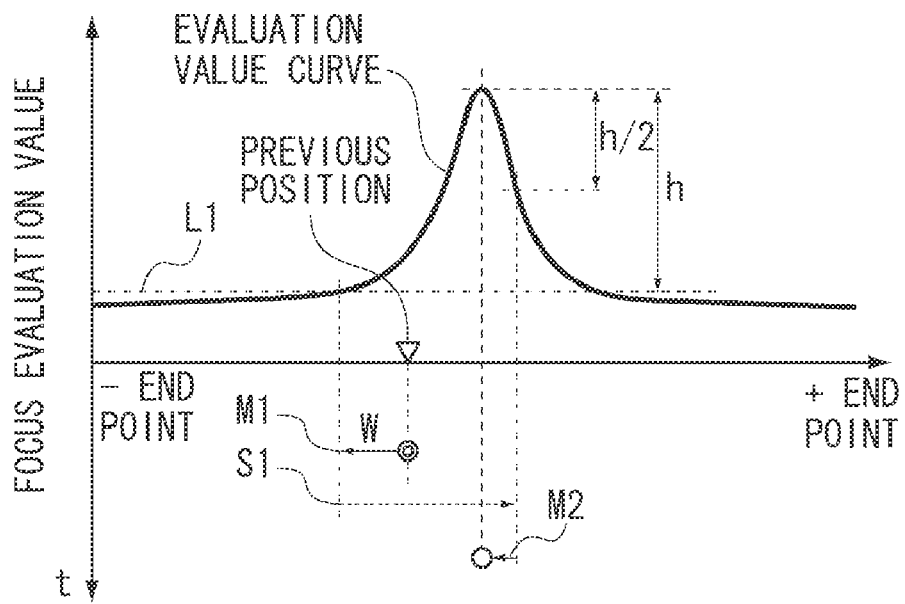
FIGS. 3A and 3B illustrate operations of a focusing lens.
Figure 3B:
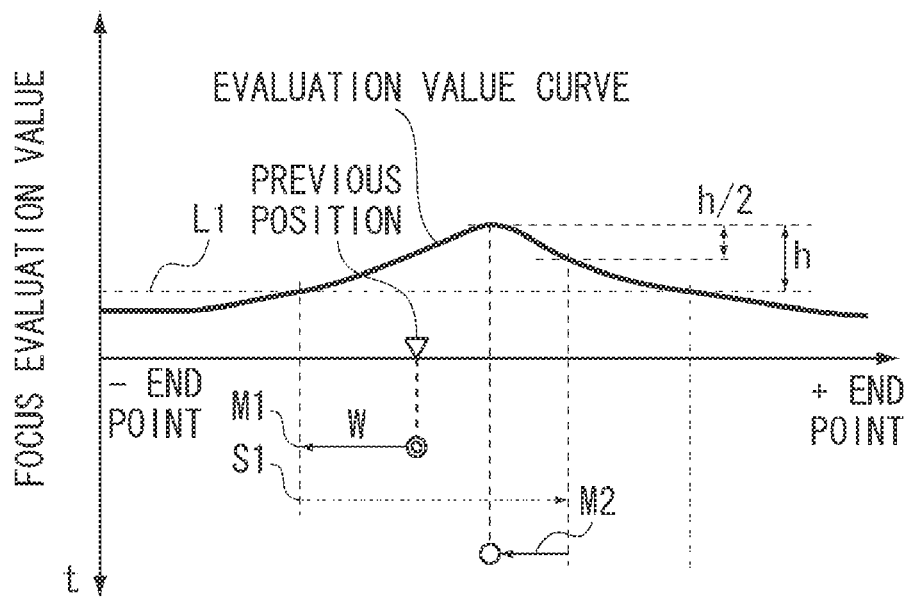
Figure 4A:
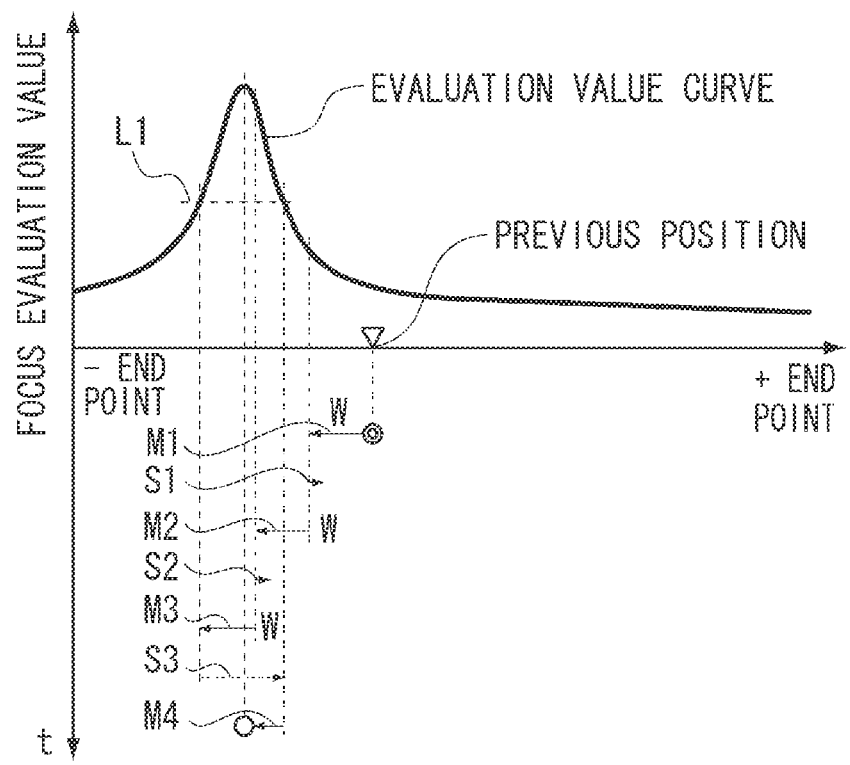
FIGS. 4A and 4B illustrate operations of a focusing lens.
Figure 4B:
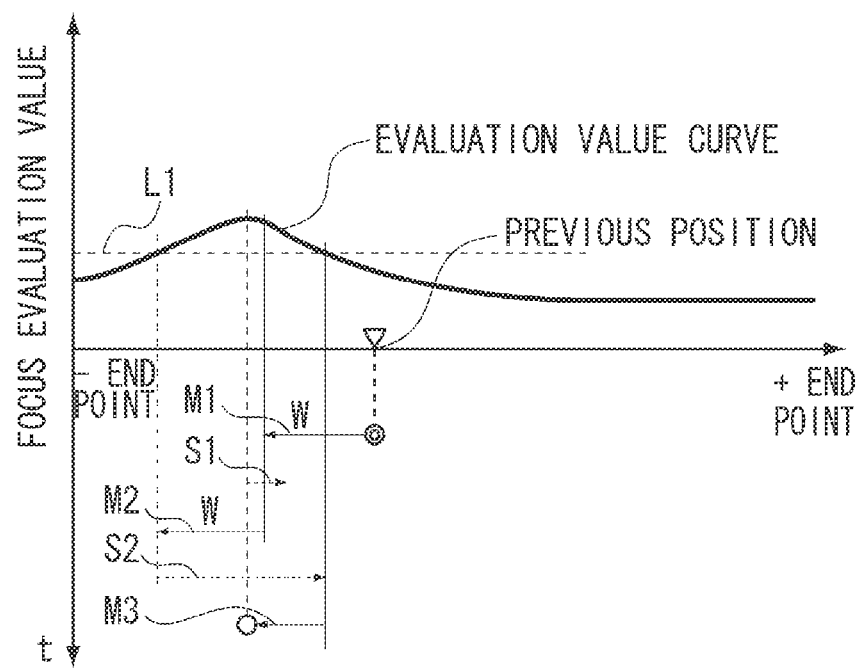

FIGS. 2A to 4B illustrate controls of a focusing lens for automatic focusing. Controls in the mydriatic mode using visible light for illumination are illustrated in FIGS. 2A, 3A and 4A, and controls in the non-mydriatic mode using near-infrared light for illumination are illustrated in FIGS. 2B, 3B and 4B. Throughout the figures, the same symbols have the same meaning respectively.

The horizontal axis represents a moving range of the focusing lens 4, with the + end point to the right hand side and the – end point to the left hand side. The vertical axis on the + side represents focus evaluation value, whereas the vertical axis on the – side represents time when the focusing lens 4 is driven. The inverted triangle mark represents a previous position of the focusing lens 4, the double circle mark represents a position where a current sequence for driving the focusing lens 4 starts, and the ○ (circle) mark represents a position where focusing is completed.

Each of the solid lines represents a simple movement of the focusing lens 4, whereas each of the broken lines represents a movement with scanning for obtaining focus evaluation values of the focusing lens 4. The mark L1 illustrates a threshold as a level of a focus evaluation value for determining positions where the focusing lens 4 is stopped or returned.

FIGS. 2A and 2B each illustrate an evaluation value curve (i.e., a curve for focus evaluation values) over the entire range scanned by the focusing lens 4. Actually, however, the range between the vertical broken lines is scanned for sampling focus evaluation values, and the curve only for the range is obtained. The mark W means a movement of a predetermined distance by the focusing lens 4.

FIGS. 2A and 2B each illustrate a control of a focusing lens according to the photographing modes, in the case where an eye to be photographed has a less refractive power as compared to that in a previous photographing.

In FIG. 2A (in the mydriatic mode) when the photographing switch 50 is half pressed, the focusing lens moves the distance W (M1) in the – direction from the position with the double circle, and the focus evaluation value at the position is set to a threshold (L1). Then, the focusing lens returns in the + direction to start scanning for focus evaluation values (S1). When the obtained focus evaluation value become equal to or less than the threshold, and a peak value is detected, the focusing lens stops the scanning, and moves back in the – direction to the peak position (M2), and stops there (at the circle-mark position).

At this point of time, the focusing control is completed, which is notified to the operator by a display (not illustrated) or sound. The operator watches and observes the LCD monitor 44 to determine whether or not the target fundus site is displayed on the monitor. If so, the operator fully presses the photographing switch 50 to cause the xenon tube 23 to emit light for photographing a still image of the fundus.

Photographing in the non-mydriatic mode will be described with reference to FIG. 2B. In the description, the position where the focusing lens 4 starts to move, and the fundus to be photographed are the same as those in the above-described mydriatic mode.

First, the focusing lens moves the distance W in the – direction. The distance W is longer than that in the mydriatic mode. In the non-mydriatic mode using near-infrared light for fundus illumination, a fundus image to be photographed has a lower contrast, and thereby focus evaluation values to be obtained are smaller than those in the mydriatic mode using visible light.

The obtained focus evaluation values produce a curve that has a profile with a lower peak and longer trails. Accordingly, an accurate detection of an in-focus position requires scanning within a larger width. The focusing lens 4 moves the distance W (M1) in the – direction and stops there. The focus evaluation value at the stopped position is set to a threshold (L1). Then, the focusing lens 4 returns to the + side to start scanning for obtaining focus evaluation values (S1). The remaining operations for focusing are the same as those in the mydriatic mode.

Figure 5A:
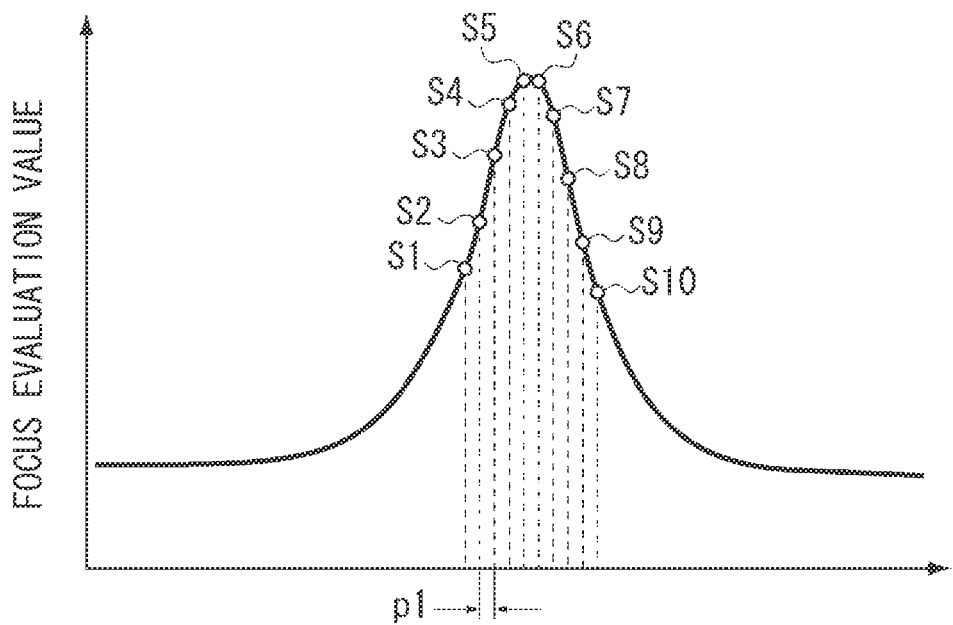
FIGS. 5A and 5B illustrates a scanning for obtaining focus evaluation values.

The difference in scanning for obtaining focus evaluation values between in the mydriatic mode and in the non-mydriatic mode will be described with reference to FIGS. 5A and 5B. FIG. 5A illustrates a curve in the mydriatic mode. The horizontal axis represents the amount of movements of the focusing lens 4, whereas the vertical axis represents the focus evaluation value. The focus evaluation values S1 to S10 are obtained for every pitch p1 as the focusing lens 4 moves.

In the mydriatic mode using visible light for fundus illumination, a fundus image to be photographed has a higher contrast, and the obtained focus evaluation values produce a curve that has a sharp profile. Accordingly, an accurate detection of an in-focus position requires scanning within a small width (i.e., the distance the focusing lens moves) at a low speed.

Figure 5B:
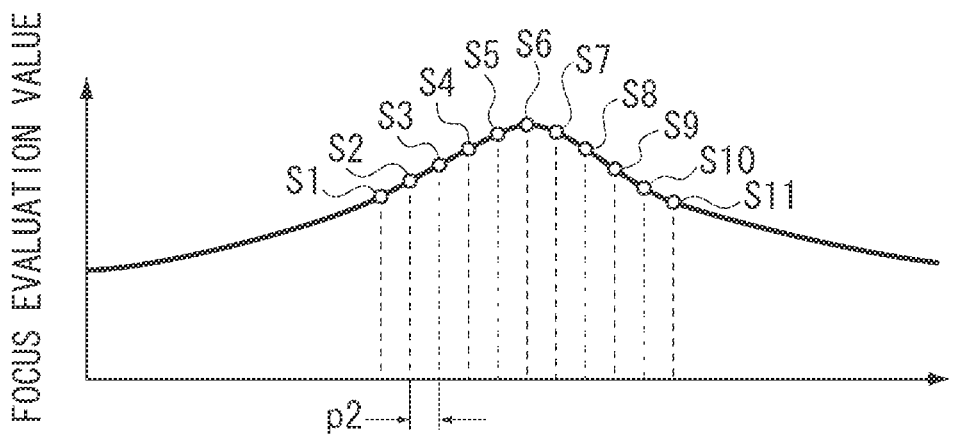

In FIG. 5B for the non-mydriatic mode, the focus evaluation values S1 to S11 are obtained for every pitch p2 as the focusing lens 4 moves. Since the fundus is illuminated with near-infrared light, a resulting fundus image has a lower contrast. As a result, the obtained focus evaluation values produce a curve of a gently sloping profile.

Accordingly, focus evaluation values may be obtained at wider pitches than those in the mydriatic mode, which increases the distance for scanning. Fortunately, the scanning can be achieved at a higher speed than that in the mydriatic mode, and the total periods of time for scanning for focusing are equal to each other in these modes.

FIG. 3 illustrates a case where an eye to be photographed has a greater refractive power as compared to that in a previous photographing. The control of a focusing lens in the mydriatic mode illustrated in FIG. 3A is similarly performed as in the case of FIG. 2, except the following.

After the focusing lens 4 moves the distance W (M1) and obtains focus evaluation values, the focus evaluation value at the position is set to a threshold L1. Then, the focusing lens 4 starts scanning for focusing in the + direction (S1). When a highest focus evaluation value is detected, the difference (h) between the highest value and the threshold L1 is compared with a reference value. If the comparison indicates that the highest value is sufficiently large, the focusing lens 4 stops the scanning when a scanned value becomes smaller than the peak value by h/2, and the focusing lens 4 moves back to the position with the highest value (M2).

The operations in FIG. 3B for the non-mydriatic mode are the same as those in FIG. 3A, but the value h that is the difference between a highest value and the threshold L1 is compared to a reference value for the non-mydriatic mode, instead of the reference value for the mydriatic mode. The focus evaluation values in the non-mydriatic mode produces a curve of a gently sloping profile with an unclear peak, resulting in a lower reference value. The other control operations are the same as those in the mydriatic mode.

FIG. 4 illustrates a case where a focusing position is offset from that in a previous photographing by more than a predetermined distance W. In the mydriatic mode, the focusing lens 4 moves the distance W (M1) in the − direction. After focus evaluation value is obtained and a new threshold is set, scanning in the + direction (S1) is started.

The scanning is then stopped because the focus evaluation values continuously drop, and the focusing lens 4 moves the distance of 2 W from the start position in the − direction (M2). After focus evaluation value is obtained and a new threshold is set, scanning in the + direction (S2) is started. The scanning, however, is again stopped because the focus evaluation values continuously drop.

Then, the focusing lens 4 moves the distance of 3 W from the start position in the − direction (M3). After focus evaluation value is obtained and a new threshold is set, scanning in the + direction (S3) is started. When a highest focus evaluation value is detected and the following focus evaluation values go below the threshold, the scanning is stopped. The focusing lens 4 moves in the − direction to the peak position (M4), and the focusing control ends.

In this case, since the difference between the highest value and the threshold is below a reference value, the scanning (S3) is performed until focus evaluation value goes below the threshold. In the non-mydriatic mode, a distance W for non-mydriatic mode is used. In the non-mydriatic mode, focus evaluation values produce a gently sloping curve, and thereby an in-focus position can be determined after the movement of the distance W is repeated twice.

Figure 7:
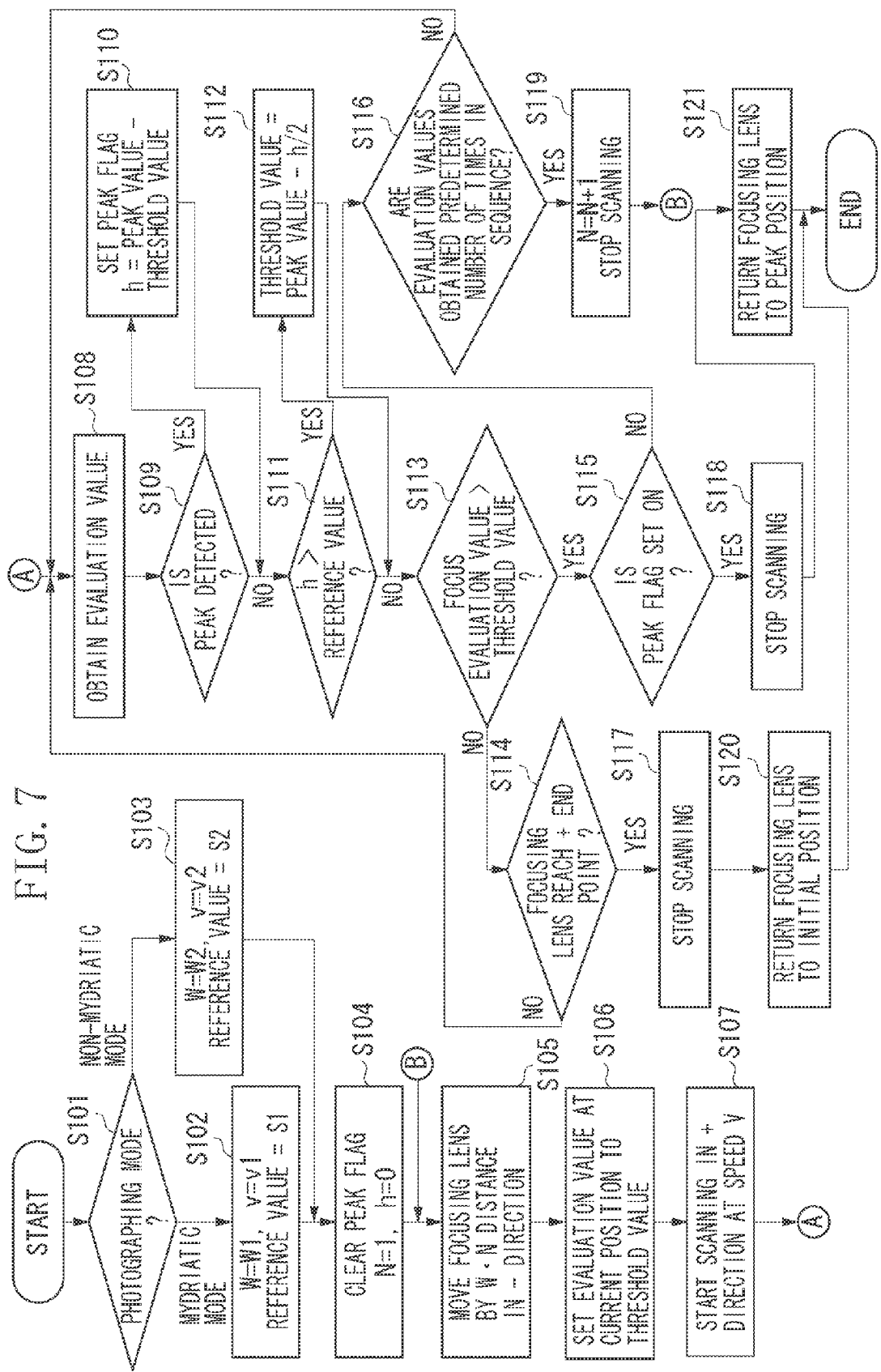
FIG. 7 is a flowchart illustrating operations according to an exemplary embodiment of the present invention.
Figure 8:
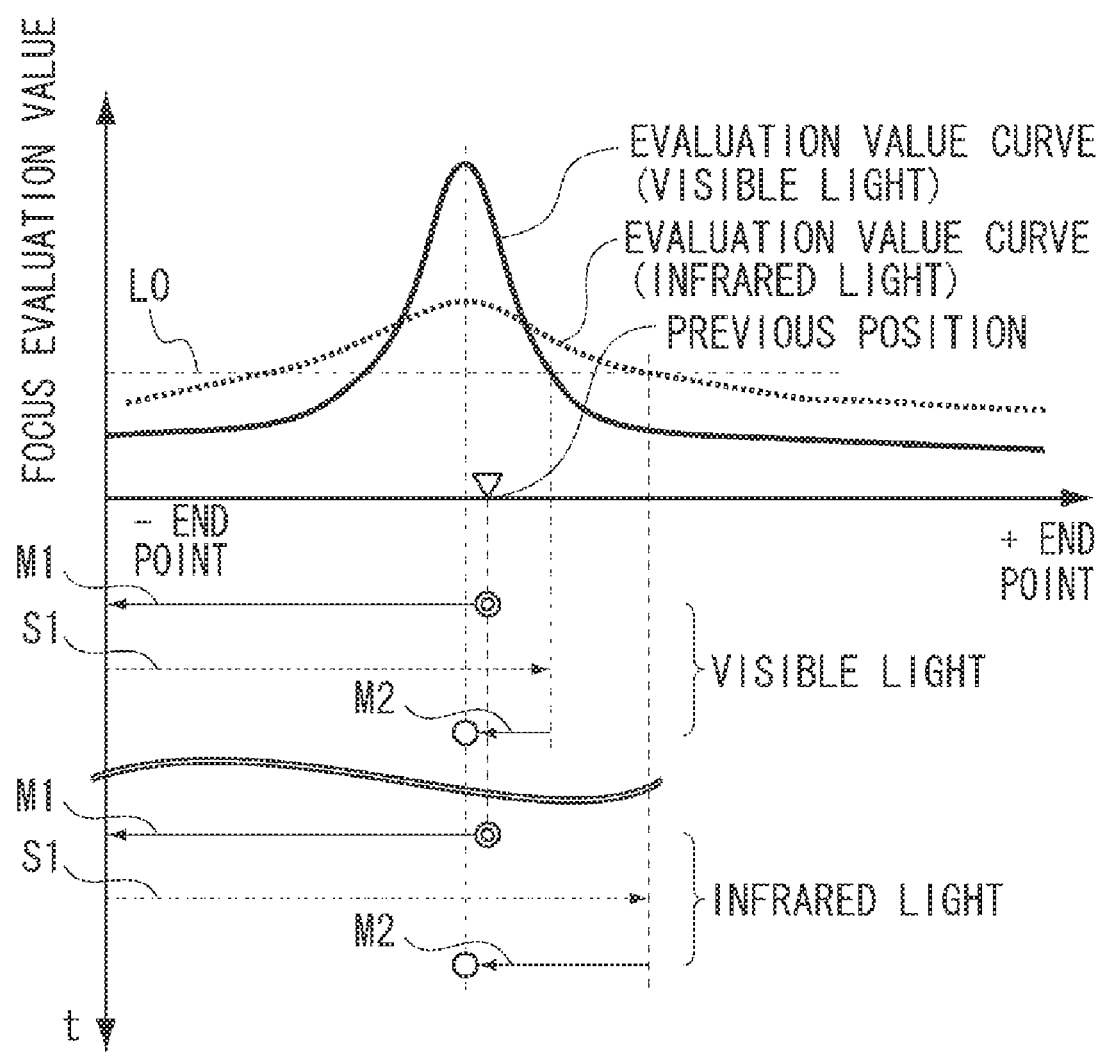
FIG. 8 illustrates operations of a conventional focusing lens.

FIG. 7 is a flowchart illustrating the focusing operations in from FIGS. 2A and 2B to FIGS. 4A and 4B. The focusing routine is performed from "START" to "END".

In step S101, a photographing mode is determined. If it is determined to be a mydriatic mode (mydriatic mode in step S101), then in step S102, a distance W1, a scan speed v1, and a reference value S1 are set. If it is determined to be a non-mydriatic mode (non-mydriatic mode in step S101), then in step S103, a distance W2, a scan speed v2, and a reference value S2 are set.

In step S104, a peak flag for storing a presence/absence of a previous peak is cleared, and the number of movement of the focusing lens N is set to 1, and the peak height h of a previous curve of focus evaluation values is cleared. In step S105, the focusing lens moves in the − direction from a starting point to a point at the distance N×W.

If the target point is beyond the − end point, the focusing lens is stopped at the − end point. In step S106, the focus evaluation value at the current position is obtained to set a new threshold. In step S107, the focusing lens starts to move in the + direction for obtaining focus evaluation values at predetermined intervals. In step S108, a focus evaluation value is obtained.

In step S109, it is determined whether or not a peak is detected. The determination is made by checking whether or not the focus evaluation value increase to the peak by a predetermined value and decrease from the peak by the predetermined value within a certain distance of the movement of the focusing lens. If a peak is detected (YES in step S109), then in step S110, a peak flag is set on, and a value h is set as a difference between the peak value of the focus evaluation value and the threshold.

In step S111, the value h is compared with the reference value, and if the value h is greater than the reference value (YES in step S111), then in step S112, a new threshold is set to a value smaller than the peak value by the value h/2. In step S113, the focus evaluation value is compared with the threshold, and if the focus evaluation value is smaller than the threshold (NO in step S113), the process proceeds to step S114, and otherwise (YES in step S113), the process proceeds to step S115.

In step S114, it is determined whether or not the focusing lens 4 has reached the + end point, and if the focusing lens 4 has not reached the + end point yet (NO in step S114), the process returns to step S108 for detecting a next peak. If the focusing lens 4 has reached the + end point (YES in step S114), then in step S117, the scanning is stopped.

In step S120, since no peak has been detected, the focusing lens 4 returns to the initial point. The initial point is approximately the center of the moving range of the focusing lens 4, and corresponds to 0 diopter.

In step S115, it is determined whether or not a peak flag is set on. If a peak is already detected (YES in step S115), in step S118, the scanning is stopped. In step S121, the focus evaluation value at each point is complemented using, for example, a spline curve to produce a curve, so that a peak of the curve is calculated, and the focusing lens 4 moves to the peak position. Then the focusing routine ends (END).

If no peak flag is set on in step S115 (NO in step S115), in step S116, it is determined whether or not focus evaluation values are obtained a predetermined number of times in a row. In other words, it is determined whether or not the obtained focus evaluation values are below the threshold continuously.

If focus evaluation values are obtained in sequence (YES in step S116), then in step S119, the number N is incremented by 1 (N=N+1) and the scanning is stopped. Then, the process returns to step S105 to repeat the process therefrom. If focus evaluation values are not obtained in sequence (NO in step S116), the process returns to step S108 to repeat the process therefrom.

In the flowchart, the focusing lens moves in the − direction, and the scanning is performed in the + direction for obtaining focus evaluation values. The directions, however, may be reversed. The values W1 and W2 and the values v1 and v2 are specified under the condition: W1<W2 and v1<v2 as described above with reference to FIG. 5. Accordingly, the predetermined distance of movement in the mydriatic mode is less than that in the non-mydriatic mode, and the scanning speed in the mydriatic mode is slower than that in the non-mydriatic mode.

There exists a method of photographing in mydriatic mode that uses visible fluorescent or a red-free light within much narrower visible wavelengths than those in color photographing. In this case, an image of a higher contrast can be obtained than that in the above described mydriatic mode, and thereby the predetermined distance of a first movement of a focusing lens can be further reduced.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-162848 filed Jul. 9, 2009, which is hereby incorporated by reference herein in its entirety.

What is claimed is:

1. A fundus camera comprising:
   an observation photographing optical system having a focusing lens for focusing an image of a fundus of a subject's eye onto an image capturing unit;
   a photographing mode selection unit configured to select a photographing mode; and
   a control unit configured to control a position of the focusing lens based on focus evaluation values calculated using the fundus image on the image capturing unit;
   wherein the control unit switches moving operations of the focusing lens according to the photographing mode.

2. The fundus camera according to claim 1, wherein the control unit changes a predetermined distance in which the focusing lens moves, according to the photographing mode.

3. The fundus camera according to claim 2 wherein, when the non-mydriatic photographing mode is selected by the photographing mode selection unit, the control unit increases the predetermined distance as compared to that when the mydriatic photographing mode is selected by the photographing mode selection unit.

4. The fundus camera according to claim 1, wherein the control unit changes a moving speed of the focusing lens according to the photographing mode.

5. The fundus camera according to claim 4 wherein, when the non-mydriatic photographing mode is selected by the photographing mode selection unit, the control unit increases the moving speed of the focusing lens as compared to that when the mydriatic photographing mode is selected by the photographing mode selection unit.

6. The fundus camera according to claim 1, wherein the control unit changes a pitch of movement of the focusing lens for obtaining the focus evaluation values, according to the photographing mode.

7. The fundus camera according to claim 6 wherein, when the non-mydriatic photographing mode is selected by the photographing mode selection unit, the control unit increases the pitch of the focusing lens for focusing as compared to that when the mydriatic photographing mode is selected by the photographing mode selection unit.

8. The fundus camera according to claim 1, wherein the photographing mode selection unit selects one of a mydriatic photographing mode where the fundus of the subject's eye is illuminated with visible light, and a non-mydriatic photographing mode where the fundus of the subject's eye is illuminated with near-infrared light.

* * * * *